United States Patent
Schomburg et al.

(10) Patent No.: US 6,594,520 B2
(45) Date of Patent: Jul. 15, 2003

(54) APPARATUS FOR PROCESSING PHYSIOLOGICAL SIGNALS

(75) Inventors: Richard A. Schomburg, Hillsboro, OR (US); Peter Thomas Bauer, West Linn, OR (US)

(73) Assignee: Biotronik Mess-und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 327 days.

(21) Appl. No.: 09/821,781

(22) Filed: Mar. 29, 2001

(65) Prior Publication Data

US 2001/0031926 A1 Oct. 18, 2001

(30) Foreign Application Priority Data

Apr. 1, 2000 (DE) .......................................... 100 17 620

(51) Int. Cl.[7] ................................................. A61B 5/04
(52) U.S. Cl. ...................................... 600/515; 600/521
(58) Field of Search ................................ 600/508, 509, 600/515, 516, 517, 518, 519, 521, 523; 128/901

(56) References Cited

U.S. PATENT DOCUMENTS

| | | | |
|---|---|---|---|
| 3,927,663 A | * 12/1975 | Russell et al. | 600/515 |
| 4,393,877 A | 7/1983 | Imran | |
| 4,807,642 A | * 2/1989 | Brown | 600/546 |
| 4,880,004 A | 11/1989 | Baker | |
| 5,354,316 A | 10/1994 | Keimel | |
| 5,381,803 A | * 1/1995 | Herleikson et al. | 600/521 |
| 5,562,709 A | 10/1996 | White | |
| 5,824,020 A | 10/1998 | Cooper | |
| 5,891,171 A | 4/1999 | Wickham | |
| 6,064,907 A | 5/2000 | Thong | |
| 6,128,526 A | * 10/2000 | Stadler et al. | 600/517 |

FOREIGN PATENT DOCUMENTS

| | | |
|---|---|---|
| DE | 196 09 365 A1 | 9/1997 |
| EP | 0 656 219 A1 | 6/1995 |
| EP | WO 00/16852 A1 | 3/2000 |
| WO | WO 00/15294 A1 | 3/2000 |

OTHER PUBLICATIONS

Dr. Lothar Wenzel, "Digitale Signalverarbeitung ist keine Hexerei," Elektronik, p. 48–53, (Mar. 1, 1999).

* cited by examiner

*Primary Examiner*—Willis R. Wolfe
(74) *Attorney, Agent, or Firm*—Hahn Loeser + Parks LLP; Stephen L. Grant (57) ABSTRACT

An apparatus for processing physiological signals, which includes a signal pick-up unit for picking up physiological measurement signals, in particular for picking up electrical signals of a heart, and first detection means which are connected to the signal pick-up unit and include signal processing means such as a filter and a first threshold value store and a comparison unit which is connected thereto and which is adapted to output a first marker signal if the amplitude of the measurement signal exceeds a threshold value stored in the first threshold value store, second detection means which are connected to the signal pick-up unit and include a second threshold value store and a second comparison unit which is connected thereto and which is adapted to output a second marker signal if the amplitude of the measurement signal exceeds a threshold value stored in the second threshold value store, and an evaluation unit which is connected to the first and second detection means for taking over a respective series of the first and second marker signals and for processing the series of marker signals to afford a single filtered series of marker signals, for analysis of the time succession of the marker signals, in particular the intervals between marker signals of the filtered series, and output of a recognition signal which is dependent on the analysis.

46 Claims, 11 Drawing Sheets

APPARATUS FOR PROCESSING PHYSIOLOGICAL SIGNALS

The invention concerns an apparatus for processing physiological signals, which includes a signal pick-up unit for picking up physiological measurement signals, in particular for picking up electrical signals of a heart, and first detection means which are connected to the signal pick-up unit and include signal processing means such as a filter and a first threshold value store and a comparison unit which is connected thereto and which is adapted to output a first marker signal if the amplitude of the measurement signal exceeds a threshold value stored in the first threshold value store, and second detection means which are connected to the signal pick-up unit and include a second threshold value store and a second comparison unit which is connected thereto and which is adapted to output a second marker signal if the amplitude of the measurement signal exceeds a threshold value stored in the second threshold value store.

BACKGROUND OF THE ART

Signal processing apparatuses of that kind can for example be a component part of a cardiac pacemaker, a cardioverter and/or a defibrillator. A specific purpose of such signal processing apparatuses is the detection of chamber fibrillation phenomena, in particular the detection of ventricular fibrillation, which require anti-tachycardia therapy or cardioversion.

In particular the detection of ventricular fibrillation phenomena, that is to say physiologically disproportionately high heart rates involves some problems. It is known in principle for the heart rates to be determined by reference to an electrocardiogram by a procedure whereby the R-spikes of the QRS-complexes contained in the electrocardiogram are detected and the frequency at which the R-spikes occur, the RR-rate, is determined. A problem in that respect involves in particular a greatly fluctuating amplitude of the R-spikes of an electrocardiogram and the differing width of the QRS-complexes.

The state of the art discloses various apparatuses for the detection of ventricular fibrillation. U.S. Pat. No. 4,393,877, to Imran, teaches providing two input channels for detecting measurement signals, which involve a differing level of sensitivity for the rise gradient of ECG-signals and linking signal features of the two channels, which are recognised by way of the rise gradient, by way of an 'exclusive-or' function. Baker, in U.S. Pat. No. 4,880,004, describes a heart stimulator which has two input channels with differing band pass characteristics, of which one serves for the detection of cardiac events and the second serves for automatic adaptation of the level of detection sensitivity of the first input channel.

White, in U.S. Pat. No. 5,562,709, teaches an atrial defibrillator having two input channels for R-spike detection, which have different band pass characteristics and which operate with respectively specific amplitude threshold values for R-spike detection. The detection results of the two input channels are logically 'and'-linked for producing a synchronisation signal. For resetting an interval timer the detection results of the two input channels are logically 'or' linked. A third separate input channel is provided for the detection of atrial fibrillation.

It has been found that the detection in particular of ventricular fibrillation, which is possible by means of the known apparatuses, leaves something to be desired in particular in terms of reliability.

Therefore the object of the present invention is to provide an apparatus for processing physiological signals, which with means of the utmost simplicity permits reliable detection of events contained in particular in cardiac signals and/or given states of the heart such as the presence of ventricular fibrillation.

SUMMARY OF THE INVENTION

In accordance with the invention that object is attained by means of an apparatus of the kind set forth in the opening part of this specification, including an evaluation unit which is connected to the first and second detection means for taking over a respective series of the first and second marker signals and for processing the series of marker signals to afford a single series of combined marker signals, for analysis of the time succession of the marker signals, in particular the intervals between marker signals of the combined series, and output of a recognition signal which is dependent on the analysis.

In the context of the invention, the recognition signal is a signal which identifies a state of the heart that is to be detected, and not an event such as an R-spike as such. Analysis of the combined series is thus not directed to the respective individual events such as R-spikes, but to the time succession of events, which is represented by the marker signals, in particular the intervals between the marker signals as a reproduction, which is already filtered, of the events. That analysis is aimed at the detection of such states as fibrillation. An apparatus of that kind advantageously makes it possible to determine RR-intervals and thus heart rates by analysis of the intervals between marker signals of a combined series of marker signals, wherein the combined series contains marker signals which originate from input channels having different detection properties. In particular an apparatus of that kind makes it possible on the one hand for the parameters of the detection means, which are crucial in terms of the detection of events and output of corresponding marker signals, such as input sensitivity, frequency characteristic and magnitude of the threshold value, and on the other hand the manner and way in which the series of marker signals obtained in two different ways are combined to form a series by suitable means to be so selected and matched to each other that the recognition of heart rates and thus also fibrillation recognition can be reliably implemented.

For analysis of the combined series of marker signals, the evaluation unit may include a counter that counts the marker signals or the intervals between marker signals within a predetermined portion of the filtered series of marker signals. That alone already makes it possible to determine the heart rate for the respective measurement signal portion. In combination with analysis of the interval lengths within the respective portion of the combined series of marker signals, it is possible to form a reliable criterion in regard to the presence of fibrillation, as is described in greater detail hereinafter.

A typical analysis is one for which a given number of for example 48 intervals is counted off and a check is made to ascertain how many of those 48 intervals are shorter than a comparison interval. A recognition signal indicating fibrillation is outputted when 36 of the 48 compared intervals are shorter than the comparison interval. In that case the evaluation unit includes for example means for counting a total number of intervals and for counting those intervals within that total number of intervals, which are shorter than a comparison interval. In addition the evaluation unit includes means for comparing the counted values to corresponding comparison values and means for outputting the recognition signal in dependence on the comparison result.

In many embodiments of the apparatus, the first selection means includes a first absolute value unit which is adapted to form the absolute value of the measurement signal. That absolute value unit may be connected upstream of the first comparison unit. In relation to the measurement signal, this means that negative measurement signal values are used with inverted signs for the threshold value comparison operation while positive measurement signal values retain their sign. It has been found that this markedly improves the reliability of fibrillation recognition.

In many embodiments, the second detection means also includes a second absolute value unit that is connected upstream of the second comparison unit.

In addition, many embodiments will be provided with a high pass filter for the measurement signal, which is either already arranged in the signal pick-up unit or which is associated with the second detection means so that the signal to be processed by the second detection means is subjected to high pass filtering with a limit frequency which is typically of an order of magnitude of 10 Hz. In that way, high-frequency interference signals are suppressed, without the band width of the signal to be processed by the second detection means being excessively greatly restricted.

Some embodiments of the second detection means have a high pass filter with a limit frequency which is typically of an order of magnitude of between 20 and 30 Hz and is thus above that of the high pass filter in the signal pick-up unit or the first detection means. The signal to be processed by the second detection means is thus frequently-limited to a greater degree than the signal to be processed by the first detection means. Such measurement signal components at a frequency of between 10 and 20 or 30 Hz are thus only processed by the first detection means.

In addition the first detection means will often have a noise limiting unit that suppresses further processing of the measurement signal within a predeterminable noise suppression time in accordance with those signal values of the measurement signal, which result in a first marker signal. In that respect each such signal value freshly triggers the first noise suppression period. The first noise suppression unit is thus retriggerable. The first noise suppression period is typically in the order of magnitude of 125 ms. The first noise suppression period is usually triggered by the rising signal edge of that signal value which exceeds the first threshold value and thus results in a first marker signal. An edge detector is appropriately provided for detection of the rising signal edge.

Many embodiments of the second detection means will have a noise limiting unit for triggering a second noise suppression period that is triggered by the rising edge of such a signal value that exceeds the second threshold value. The second detection means will also often have an edge detector. The triggered noise suppression period is retriggerable, that is to say, it is freshly triggered by each signal value which exceeds the threshold value and which also occurs within the noise suppression period. The second noise suppression period is of an order of magnitude of about 50 ms.

A typical embodiment of the first detection means will also have a refractory timer which triggers a first refractory time if a measurement signal value exceeds the first threshold value and thus triggers a first marker signal if that occurs outside the first refractory time. The refractory timer is thus not retriggerable and responds only to signals which are outside the refractory time. The first refractory time is composed of an absolute refractory time of typically 150 ms and a relative refractory time, the total refractory time typically being 300 ms. Events occurring throughout the entire refractory time of 300 ms, after detection of a signal value which exceeds the threshold value, are not taken into consideration in terms of further processing. The first refractory timer is connected downstream of the first noise limiting unit.

Some embodiments of the second detection means will also include a second non-retriggerable refractory timer for a second refractory time. The second refractory time is about 135 ms.

The edge detectors for detecting rising signal edges and triggering the first or second noise suppression period or the first or second refractory time respectively are commonly so designed that they are responsive to a threshold value-passage of the measurement signal in the positive direction.

An essential feature of the apparatus according to the invention is the evaluation unit. That is adapted to take over the series of first and second marker signals, which originate from the first and second detection means, more specifically in such a way that the time relationship between the first and second marker signals, which is given by way of the measurement signal and its signal values which exceed the threshold value and which lead to marker signals, is maintained. Taking over the series of first and second marker signals from the first and second detection means is thus effected in mutual time correlation or in mutually synchronised relationship.

In at least one alternative embodiment, the evaluation unit includes a logic unit by which the series of first and second marker signals are combined in the manner of 'or' linking to form a common series, wherein first and second marker signals which are within a time window of about +/−50 ms are combined to afford a marker signal of the combined series. That combined series will usually be filtered by a logic filter unit in such a way that the filtered series of marker signals contains only such marker signals which lie outside a masking time in the range of about 300 ms which is triggered by each marker signal of the second series of marker signals, which comes from the second detection means.

In at least one embodiment, the evaluation unit includes:
coincidence recognition means which are adapted to output a coincidence signal when one of the first marker signals falls outside the first refractory time and one of the second marker signals falls outside the second noise suppression period in a coincidence period of about 50 ms,
masking means which are connected to the coincidence recognition means and which are adapted to mask those of the second marker signals for further signal processing, which within a first masking time of about 300 ms follow a second marker signal which led to a coincidence signal,
coincidence transfer means which are connected to the coincidence recognition means and which are adapted to add the first of the first marker signals which follows a coincidence signal outside the first noise suppression period and within a transfer period of about 300 ms, while retaining the time relationship of the series of the second marker signals, and thus to form a modified series of marker signals, and
coincidence transfer masking means which are connected to the coincidence transfer means and which are adapted to mask out of the modified series of marker signals all those marker signals which within a second masking time of about 300 ms follow a marker signal added by the coincidence transfer means, in order thereby to form a filtered series of marker signals.

With an evaluation unit of that kind, a series of rules is converted into practice, resulting in an optimised combined series for further analysis.

The two alternative configurations of the evaluation unit may additionally include:

interval determining means which are adapted to determine the interval duration of time intervals between two adjacent marker signals of the filtered series of marker signals, a comparison interval store for a comparison interval time duration, interval comparison means which are connected to the interval determining means and the comparison interval store and are adapted to detect those intervals of the filtered series of marker signals, which are shorter than the comparison interval time duration, a counter which is connected to the interval comparison means and adapted to determine the number of marker signals within a portion of the filtered series of marker signals or intervals between two respective adjacent marker signals and the number of those intervals which are shorter than the comparison interval time duration, and a signal generator which is connected to the interval counting unit and a quotient store and is adapted such that the signal generator outputs a signal if the proportion of the intervals which are shorter than the comparison interval time duration exceeds a proportion, stored in the quotient store, of the total number of intervals of a portion of the filtered series.

By virtue of those means, the evaluation unit is capable of counting off a given number of intervals and determining how many of those intervals are shorter than a comparison interval. In specific terms, the evaluation unit can be so designed that the counter counts off a predetermined number of intervals, for example 48, and, by means of the interval comparison means, marks those intervals which are shorter than the comparison interval. If the number of marked intervals within the 48 intervals exceeds for example the value 36, a signal characterising fibrillation is outputted. If therefore the counter is so designed as to count in each case 48 intervals, then the signal generator can include a second counter for the intervals which are shorter than the comparison interval. The quotient store then stores a limit value for the number of those shorter intervals and the signal is triggered if the value in the second counter exceeds the value stored in the quotient store. In other words, if the denominator of the quotient, for example 48, is predetermined by the first counter, the quotient store of the signal generator only has to include the numerator of the quotient, for example 36. Other per se known means which provide that the evaluation unit outputs a signal if out of for example 48 last-detected intervals more than 36 are shorter than a comparison interval, are also suitable for implementation of alternative configurations of the evaluation unit.

Some embodiments of the signal pick-up unit include a decimator that samples the measurement signal at a first rate and outputs sample values for the measurement signal at a second rate, with the first rate typically eight times as fast. That permits sampling of the measurement signal with an adequate degree of accuracy and results in a first data reduction which significantly restricts complication and expenditure in terms of further processing of the measurement signal.

Many embodiments of the signal pick-up unit also include an analog/digital converter for the measurement signal so that the measurement signal is converted into a series of time-discrete, digital values which can be subjected to further digital processing.

Some signal pick-up units will include averaging means for forming a sliding average of the measurement signal. That provides for suppressing dc signal components of the measurement signal, which are possibly subjected to drift, prior to further processing by the two detection means.

Some first detection means will have a signal amplifier for the measurement signal with an adaptable gain factor. In the case of a heart stimulator the gain factor is should be increased if the stimulator delivers a stimulation pulse. In addition or as an alternative the gain factor is also increased if the second detection means have detected, within 200 ms prior to delivery of the stimulation pulse, a signal value which exceeds the second threshold value and thus results in a second marker signal.

The second detection means should be designed to be such that they can be switched off and are activated by an activation unit if the gain factor of the signal amplifier of the first detection means is increased.

Alternatively or in addition the activation unit also activates the second detection means if the signals detected by the first detection means exceed a frequency of 140 signals per minute.

The second detection means can be designed for time-shifted processing of the measurement signal values and for that purpose often includes a signal store for the digitised measurement signal which is outputted by the averaging means. That signal store can be in the form of a ring store or first-in, first-out store (FIFO-store).

BRIEF DESCRIPTION OF THE DRAWINGS

The invention will now be described in greater detail by means of an embodiment with reference to the Figures in which.

DETAILED DESCRIPTION OF THE INVENTION

Figure 1:
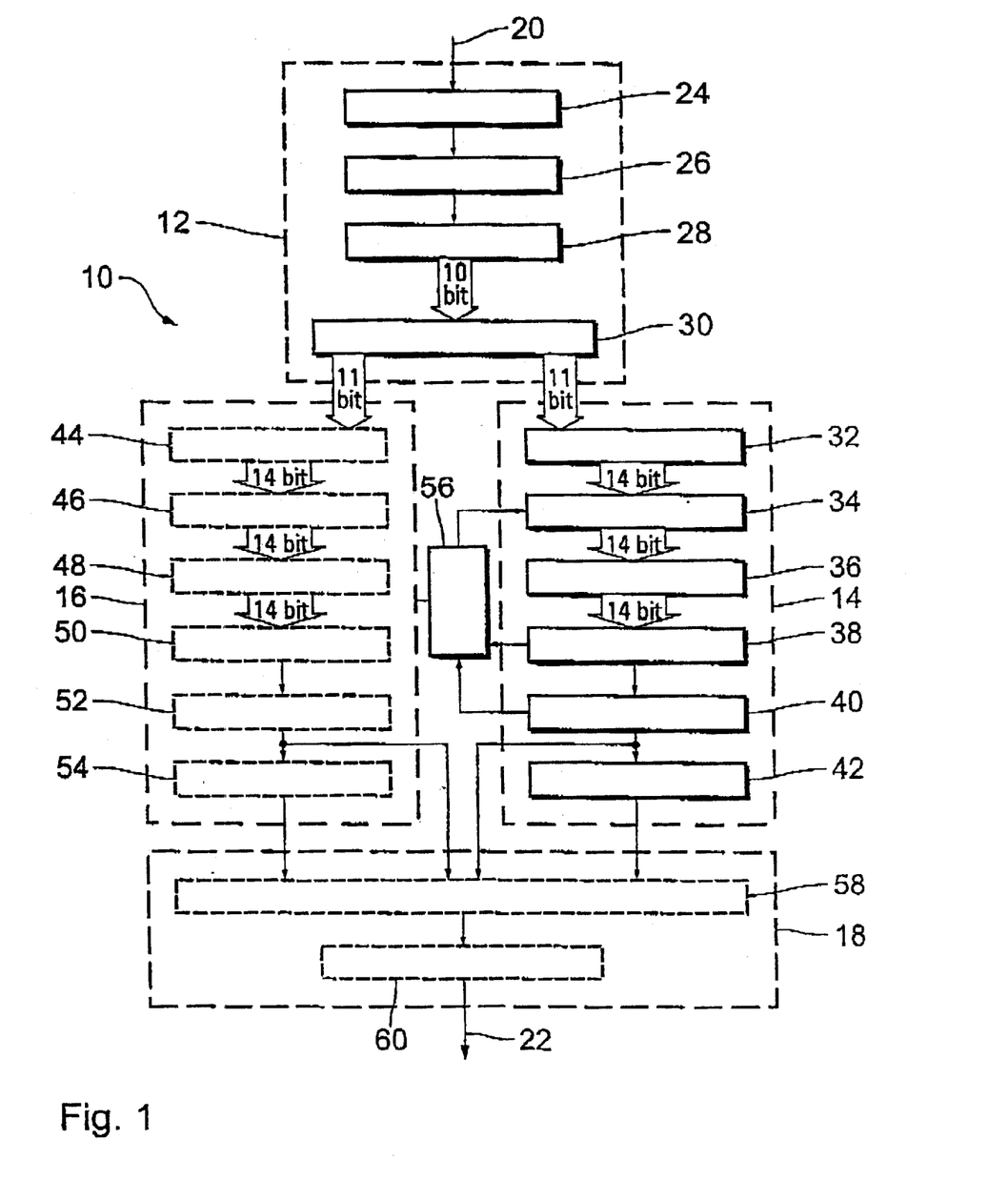
FIG. 1 shows a block diagram of an embodiment of a signal processing apparatus.

Referring to the block diagram of the signal processing apparatus 10 in FIG. 1, it can be seen therefrom that the signal processing apparatus 10 includes as four essential component parts a signal detection or pick-up unit 12, first detection means 14, second detection means 16 and an evaluation unit 18. Applied to a measurement input 20 is an electrical signal which corresponds to an electrocardiogram of a heart. The signal can be a test signal or it can be picked up intracardially. By way of a signal output 22 the signal processing apparatus 10 then delivers an output signal if the signal processing apparatus 10 has detected fibrillation by means of the above-described component parts thereof, on the basis of the measurement signal.

The signal pick-up unit 12 has the measurement input 20 at the input side thereof and at the output side is connected to the first detection means 14 and the second detection means 16. Component parts of the signal processing unit 12 are an anti-aliasing filter 24 connected to the measurement input 20. On the output side the anti-aliasing filter is connected to a decimator 26 which in turn is connected to an analog/digital converter 28. The measurement signal is subjected to analog processing, as far as the analog/digital converter 28. On the output side the analog/digital converter 28 is connected to an averaging filter 30 for sliding averaging. The averaging filter 30 has two identical outputs which go to the first detection means 14 on the one hand and to the second detection means 16 on the other hand.

The anti-aliasing filter 24 is a passive, hybrid band pass R-C filter with a frequency characteristic (−3 dB) of between 10 Hz and 224 Hz. The decimator 26 is a decimator with switching capacitors with an input sampling rate of 4096 Hz and an output data rate of 512 Hz. It has a programmable gain of between 20/9 and 80/9. Each output value is the sum of 8 input sampling values, multiplied by the gain factor. The analog/digital converter 28 is designed for an input voltage of between −500 mV and +500 mV and at the output side affords a data resolution of 10 bits in two's complement representation. The averaging filter 30 calculates a sliding average in such a way that each output value is the sum of the current and the preceding input values. It has a gain factor of 2 and a data resolution at the output of 11 bits.

The first detection means 14 include the following component parts: a high pass filter 32, a programmable amplifier 34, an absolute value unit 36, a threshold value detector 38, a noise limiter 40 and a refractory timer 42. Those components parts are connected in series in the sequence listed, that is to say the output of a previously mentioned component part is connected to the input of the respective next-mentioned component part. The high pass filter 32 is a second-order Butterworth high pass filter with a data resolution at the output of 14 bits and a limit frequency of 18 Hz. Its gain factor is 8. The programmable amplifier 34 is programmable in regard to the gain factor. The level of input sensitivity can be set in fifteen stages between 0.5 mV and 7.5 mV. With a level of sensitivity of 5 mV the gain factor is 2.1875. The absolute value unit 36 converts an input signal between positive and negative values at the input side into an output signal whose signal values correspond to the magnitude of the input signal values. Accordingly negative signal values of the input signal are converted into positive signal values of the same magnitude of the output signal while positive input signal values remain unchanged. The threshold value detector 38 outputs a signal 1 for each input value which exceeds a stored threshold value of 850. Otherwise the threshold value detector 38 outputs no output signal or logic '0'. The noise limiter 40 masks out all signal values of the threshold value detector 38, which within 125 ms follow a rising signal edge of the measurement signal, which results in the threshold value being exceeded. The noise limiter 40 is thus edge-triggered and retriggerable, that is to say, events occurring within the masking time of 125 ms also freshly trigger the masking time and thus prolong it. As a rising edge of the measurement signal, in the event of the threshold value being exceeded, results in the output signal of the threshold value detector jumping from 0 to 1, the masking time is triggered by the signal edge, which jumps from 0 to 1, of the output signal of the threshold value detector 38. The refractory timer 42 triggers a non-retriggerable masking time of 300 ms which begins with a rising edge of the output signal of the threshold value detector 38 upon the change from logic '0' to logic '1'. As that masking time of 300 ms is not retriggerable, events within that refractory time do not result in a prolongation of the refractory time.

The second detection means 16 include a scaling device 44, a programmable amplifier 46, an absolute value unit 48, a threshold value detector 50, a noise limiter 52 and a refractory timer 54. Those components are also connected in series in the succession in which they are listed so that the output of a first-mentioned component is connected to the input of the next-mentioned component. In many situations, the components of the second detection means 16 are implemented in software form. For that purpose, a ring store or an FIFO-store (FIFO=first-in, first-out) can be provided between the averaging filter 30 and the scaling device 44 in order to provide for intermediate storage of a respective current signal portion of the output signal of the averaging filter 30, for further processing. That signal processing by the second detection means 16 then does not need to be effected in real time. It is however effected in strictly synchronised relationship with signal processing by the first detection means 14.

The scaling device 44 scales the output signal of the averaging filter 30 by the factor 8. Accordingly with an 11 bit input signal the scaling device 44 has a 14 bit output signal. That is amplified by the programmable amplifier 46 whose gain factor is so set that it corresponds to the initial gain factor of the programmable amplifier 34 of the first detection means 14.

The absolute value unit 48 forms from an input signal with positive and negative signal values an output signal with exclusively positive signal values whose magnitude corresponds to that of the input signal values. The threshold value detector 50 outputs an output signal when the input signal exceeds a stored threshold value of 300. When the threshold value is exceeded the output signal of the threshold value detector 50 changes from logic '0' to logic '1'. The edge of the threshold value detector 50, which rises from logic '0' to logic '1', causes the noise limiter 52 to trigger a retriggerable masking or noise suppression time duration of 50 ms. That masking time is thus shorter than the corresponding time of the first detection means. It is prolonged with each event which occurs during the masking time. The refractory timer 54 triggers a non-retriggerable masking or refractory time of 135 ms at each edge of the threshold value detector 50, which rises from 0 to 1 and which occurs outside the refractory time of 135 ms.

Figure 3:
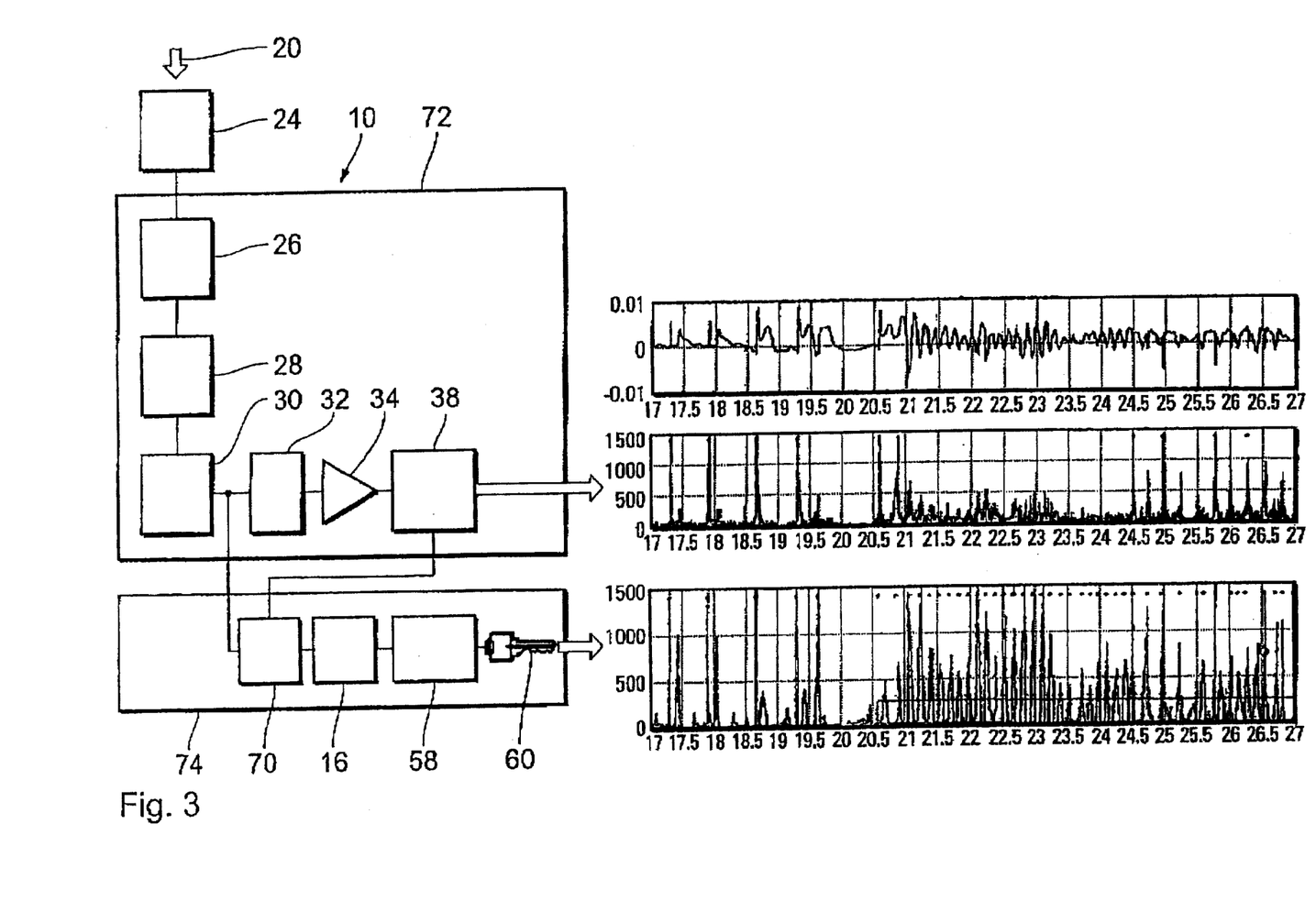
FIG. 3 shows a simplified view of the apparatus of FIG. 1 and a measurement signal and the signals outputted by the first and second detection means.

As indicated in FIG. 3 the first detection means 14 are connected to the second detection means 16 in such a way that the first detection means 14 start the second detection means 16 only when the first detection means detect a heart rate which is above 140 beats per minute. Such triggering or starting of the second detection means 16 is retriggerable. In addition the second detection means 16 are started by the first detection means 14 when the gain factor of the programmable amplifier 34 is adapted. The second detection means 16 are switched off again if fibrillation were detected or if they were not started again within 30 seconds. Adaptation of the gain factor of the programmable amplifier 34 occurs whenever the threshold value detector 38 does not detect any events within a predetermined interval and in addition events triggering or retriggering the noise limiter have occurred within the respective last 200 ms. The gain factor is reduced by a step if retriggering, that is to say re-starting of the noise limiter 40, occurs by virtue of an event within the masking or noise suppression time duration. For implementing the functions described in this paragraph, there is provided a suitably designed control logic 56 which is connected both to the first detection means 14, in particular the programmable amplifier 34, the threshold value detector 38 and the noise limiter 40, as well as the second detection means 16.

The output signals of the noise limiter 40 and the refractory timer 42 of the first detection means 14 and the output signals of the noise limiter 52 and the refractory timer 54 of the second detection means 16 are fed to the evaluation unit 18. The evaluation unit 18 includes a coincidence unit 58 and an identification unit 60. The coincidence unit 58 is connected to the noise limiter 50 and the refractory timer 42 of the first detection means 14 and the noise limiter 52 and the refractory timer 54 of the second detection means 16. On the output side the coincidence unit 58 delivers a signal to the identification unit 60. The output signal of the identification unit 60 is the fibrillation-characterising output signal of the signal processing apparatus 10 and the output 22 thereof.

Figure 2:
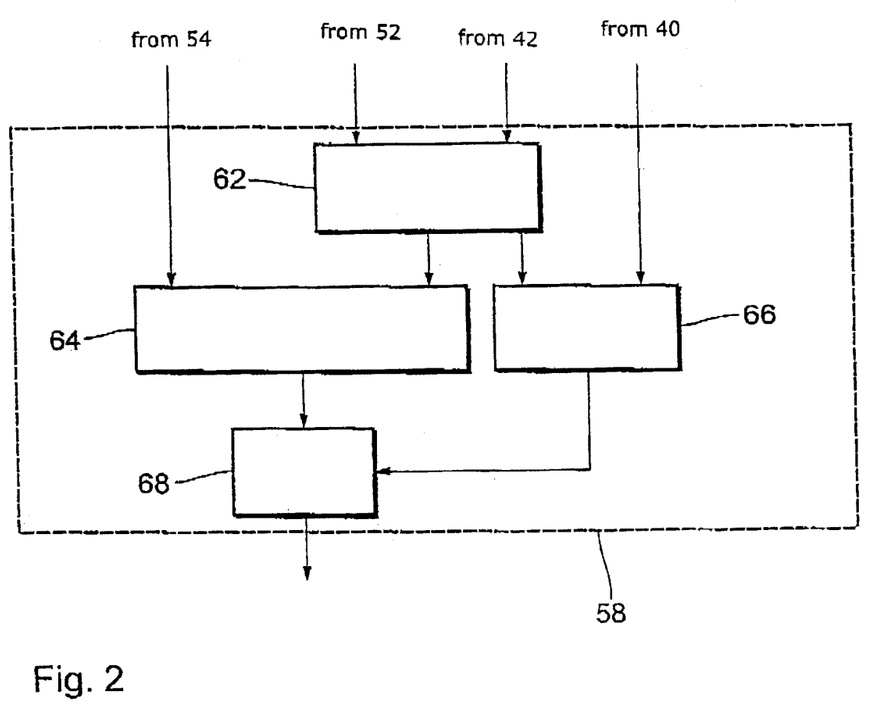
FIG. 2 shows a detail view of the evaluation unit of the signal processing apparatus of FIG. 1.

The internal structure of the coincidence unit 58 is shown in greater detail in FIG. 2. A coincidence recognition unit 62 is connected to the refractory timer 42 of the first detection means 14 and the noise limiter 52 of the second detection means 16. The coincidence recognition unit 62 is so designed that a coincidence signal occurs at the output thereof if an output signal (logic '1') of the refractory timer 52 of the second detection means 16 occurs within a period of 50 ms before an output signal of the noise limiter 42 of the first detection means 14. The output signal of the coincidence recognition unit 62 is delivered as a coincidence signal both to a masking unit 64 and also to a coincidence transfer unit 66.

The masking unit 64 is connected at the input side therefore both to the coincidence detection unit 62 and also to the refractory timer 54 of the second detection means 16. The masking unit 64 is so designed that it masks all those output signals (logic '1') of the signal series outputted by the refractory timer 54, which within 300 ms follow a coincidence signal outputted by the coincidence recognition unit 62. The output signal of the masking unit 64 is thus a signal series which originally comes from the second detection means 16 and out of which the masked signal values are filtered.

The coincidence transfer means 66 are connected on the input side to the coincidence recognition unit 62 and the noise limiter 40 of the first detection means 14. The coincidence transfer unit 66 is so designed that an output signal (logic '1') coming from the noise limiter 40 occurs at the output of the coincidence transfer means 66 if within 300 ms it follows a coincidence signal outputted by the coincidence detection unit 62. Precisely as at the output of the masking unit 64, a signal series also occurs at the output of the masking unit 66. The two signal series are synchronised with each other by way of the input or measurement signal. The two signal series occur at the input of a coincidence transfer masking unit 68 which is so designed that the signals of the signal series coming from the coincidence transfer unit 66 are added to the signal series coming from the masking unit 64 and all signals of the signal series which come from the masking unit 64 and which within 300 ms follow an added signal coming from the coincidence transfer unit 66 are masked out. The signal series which is modified in that way occurs at the output of the coincidence transfer masking unit 68 and at the same time at the output of the coincidence unit 58. The output of the coincidence transfer masking unit 68 and thus the output of the coincidence unit 58 are connected to the input of the identification unit 60.

The identification unit 60 includes counters for counting intervals between the signals (marker signals) of the signal series which is taken over from the coincidence transfer masking unit 68. In addition the identification unit includes an interval duration determining device and an interval comparison device which is connected thereto. The interval comparison device has access to a stored value for a comparison interval time duration and marks all those intervals of the signal series, which are shorter than the comparison interval. The identification unit 60 is further so designed that by means of the counters it counts off a predeterminable number of for example 48 intervals and at the same time counts off the marked intervals, within those 48 intervals, which are shorter than the comparison interval time duration. A further comparison unit of the identification unit 60 continuously compares the number of the marked intervals within the 48 last-counted intervals and compares the number of the marked intervals to a stored comparison value of for example 36. If the number of marked intervals is greater than 36 then the identification unit 60 outputs a fibrillation recognition signal by way of the signal output 22 of the signal processing apparatus 10. Accordingly, the criterion in regard to the output of that fibrillation recognition signal is that at least 36 of the 48 most recent intervals between the signals of the signal series taken over from the coincidence transfer masking unit are shorter than the comparison interval time duration.

FIG. 3 serves to illustrate by way of example the mode of operation of the signal processing apparatus 10. The left-hand side of FIG. 3 shows an alternative configuration of the signal processing apparatus 10 illustrated in FIG. 1. The component parts which have already been described are denoted by identical references. Additionally shown therein is a ring or FIFO store 70 which is already mentioned in the description referring to FIG. 1 but which is not shown in FIG. 1 itself. The identification unit 60 is illustrated in the form of a key. The block 72 includes the component parts of the signal processing apparatus 10, which are implemented in hardware form, and the block 74 includes the apparatus components which are implemented in software form. These involve program modules which are stored in a program store or memory of the signal processing apparatus 10 and which are processed by a microprocessor (not shown).

Shown in the uppermost part on the right-hand side in FIG. 3 is a measurement signal as is applied by way of example at the input 20 of the signal processing apparatus 10. Shown therebeneath is the measurement signal which has been subjected to preliminary processing by the signal pick-up unit 12 and the high pass filter 30, the programmable amplifier 34 and the absolute value unit 36, as is applied to the input of the threshold value detector 38. The upper edge of the same diagram shows the first marker signals which are outputted by the threshold value detector 38 and which the threshold value detector 38 outputs whenever the pre-processed measurement signal which is applied to its input and which is shown in the same diagram exceeds the programmed threshold value.

The third diagram which is shown in the lowermost part on the right-hand side of FIG. 3 illustrates on the one hand the measurement signal which has been subjected to preliminary processing by the signal pick-up unit 12 and the subsequent components of the second detection means 16, as is applied to the input of the threshold value detector 50. Entered at the upper edge of the same diagram are the marker signals which the threshold value detector 50 outputs whenever the measurement signal which has been processed by the second detection means 16 exceeds the programmed threshold value. The second and third diagrams on the right-hand side of FIG. 3 therefore also show, besides the respective pre-processed measurement signal, the series of first and second marker signals, which are outputted by the first and second threshold value detectors respectively.

Figure 4:
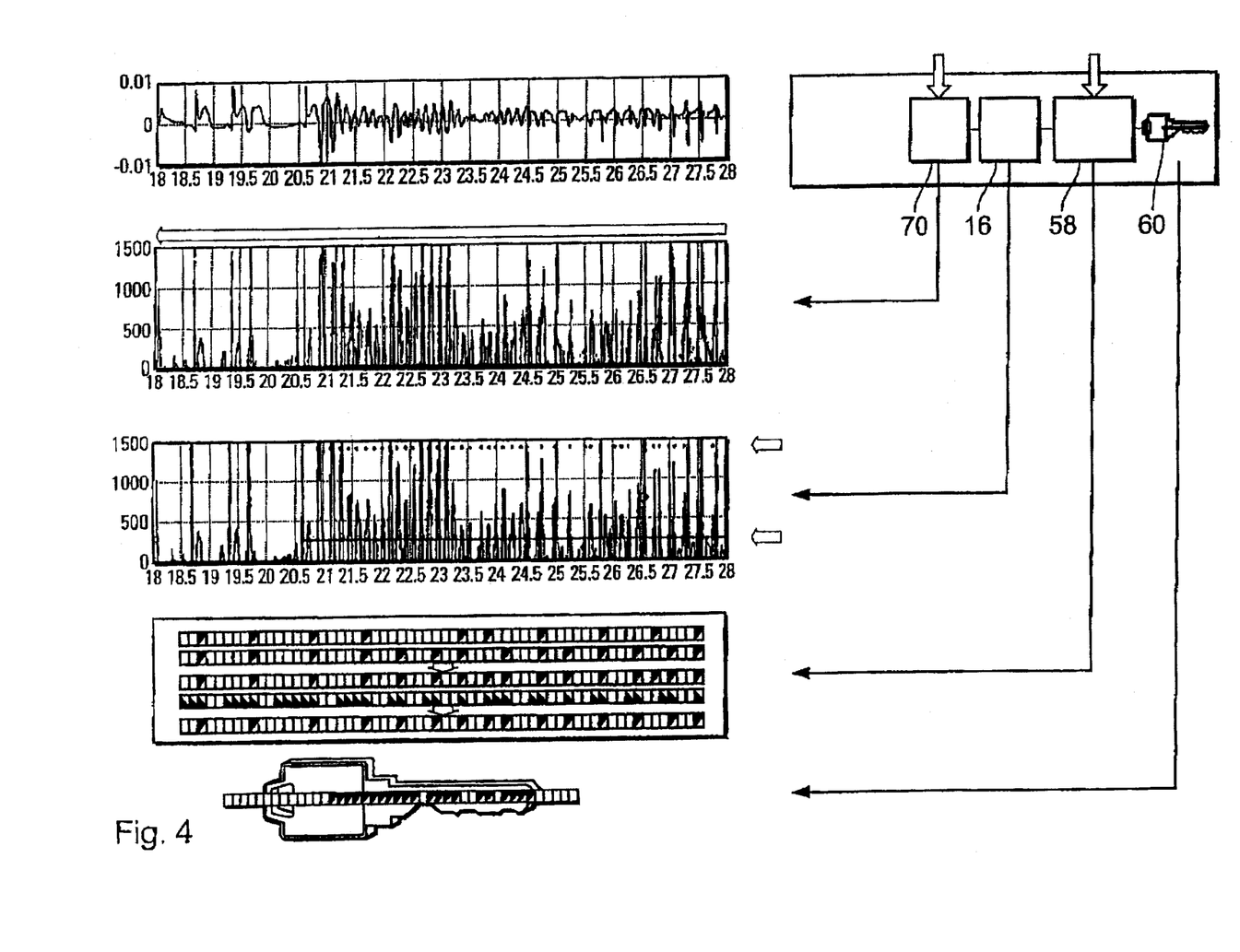
FIG. 4 shows a view similar to FIG. 3.

These are subjected to further processing by the coincidence unit 58 and the identification unit 60. That is shown in FIG. 4. The left-hand side of FIG. 4 shows 4 diagrams of which the uppermost one shows the measurement signal and corresponds to the uppermost diagram on the right-hand side in FIG. 3. Shown therebeneath is the signal portion which is stored in the ring store 70, as is outputted by the signal pick-up unit 12 and serves as an input signal for the second detection means 16. Shown therebeneath are the preprocessed measurement signal which occurs at the threshold value detector 50, and the marker signals outputted by the threshold value detector 50. The third diagram on the left-hand side in FIG. 4 thus corresponds to the third diagram on the right-hand side in FIG. 3. The fourth diagram on the left-hand side in FIG. 4 is a diagrammatic representation of the series of marker signals, as occur at various processing stages in the coincidence unit 58. The fourth diagram on the left-hand side in FIG. 4 is shown on an enlarged scale in FIG. 5. Finally, the key shown in FIG. 4 and FIG. 5 represents signal processing in the identification unit 60.

Figure 5:
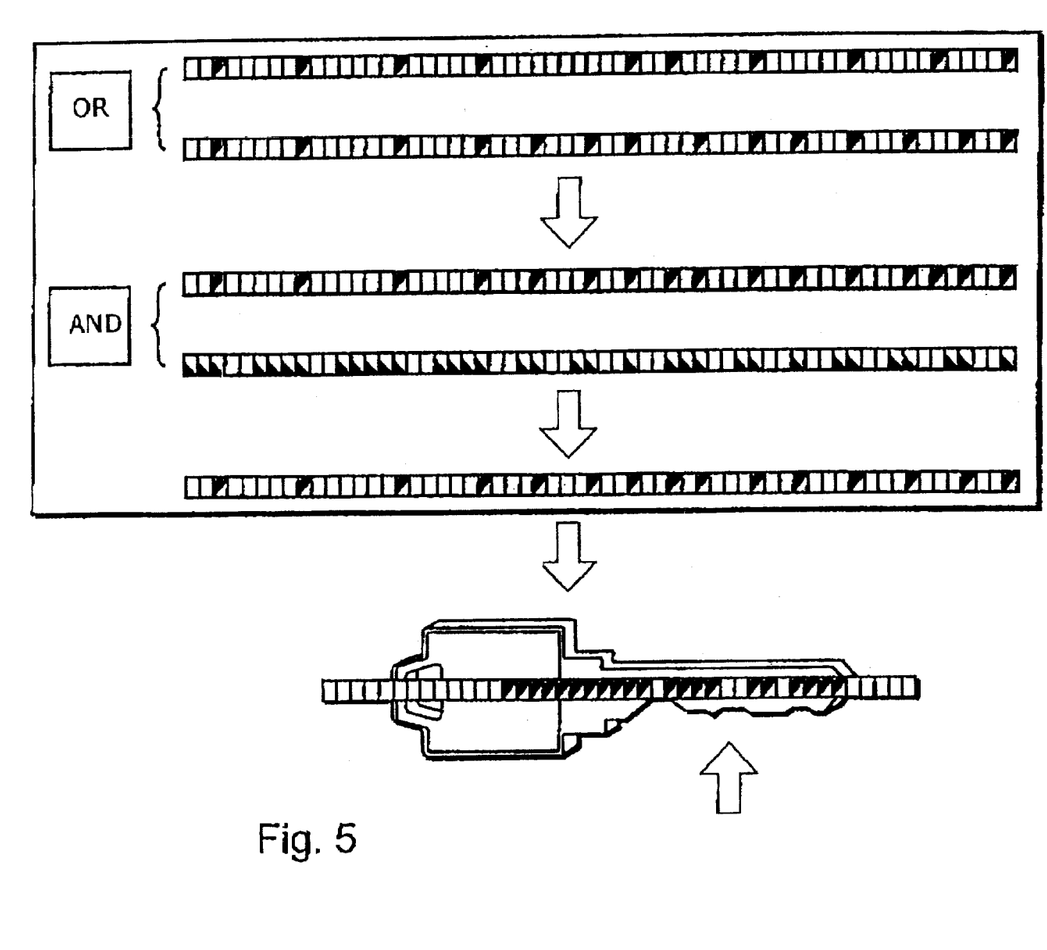
FIG. 5 shows a diagrammatic view to illustrate the mode of operation of the evaluation unit.
Figure 6:
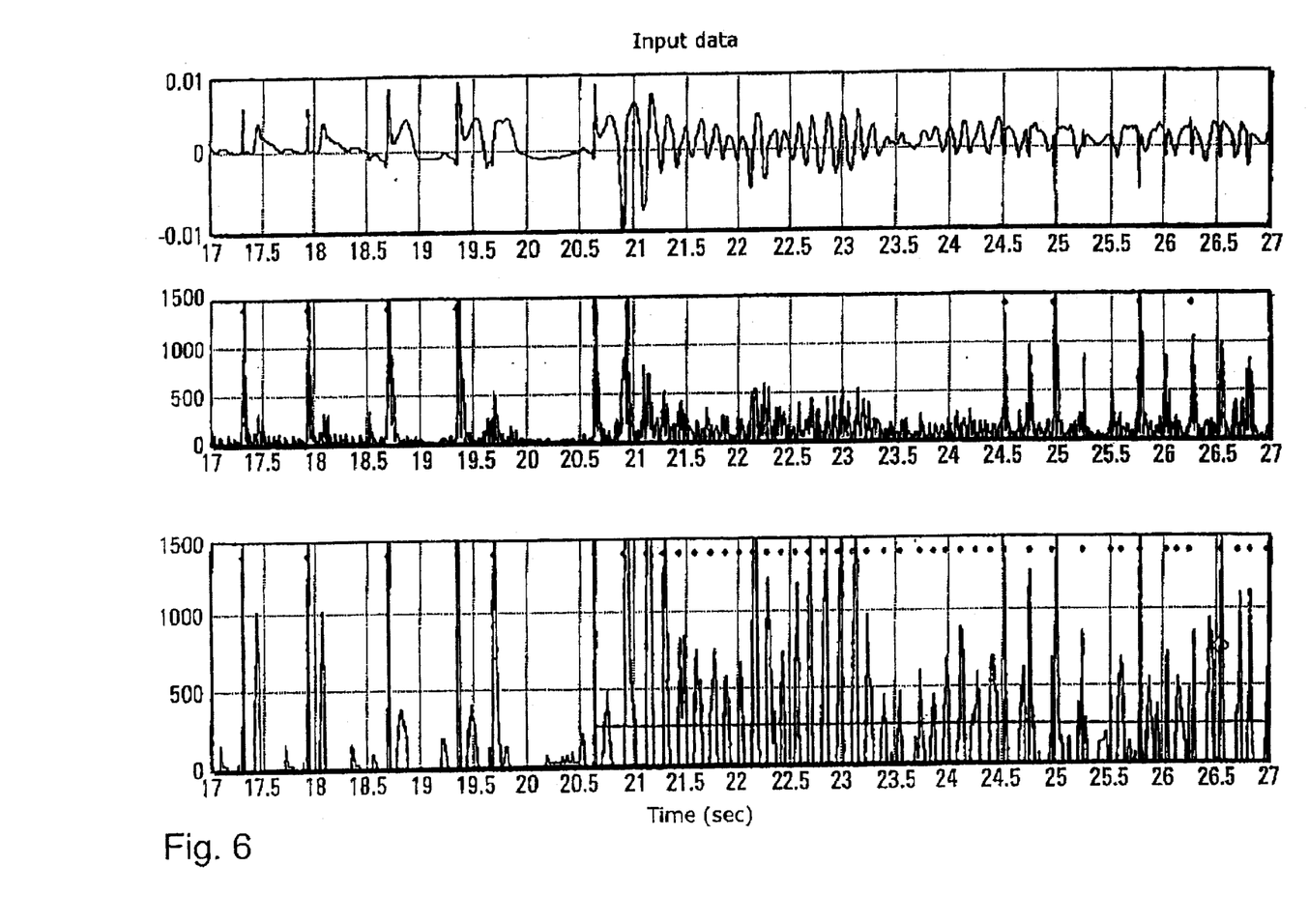
FIGS. 6 through 11 show various measurement signals and the corresponding signals of the first and second detection means.
Figure 7:
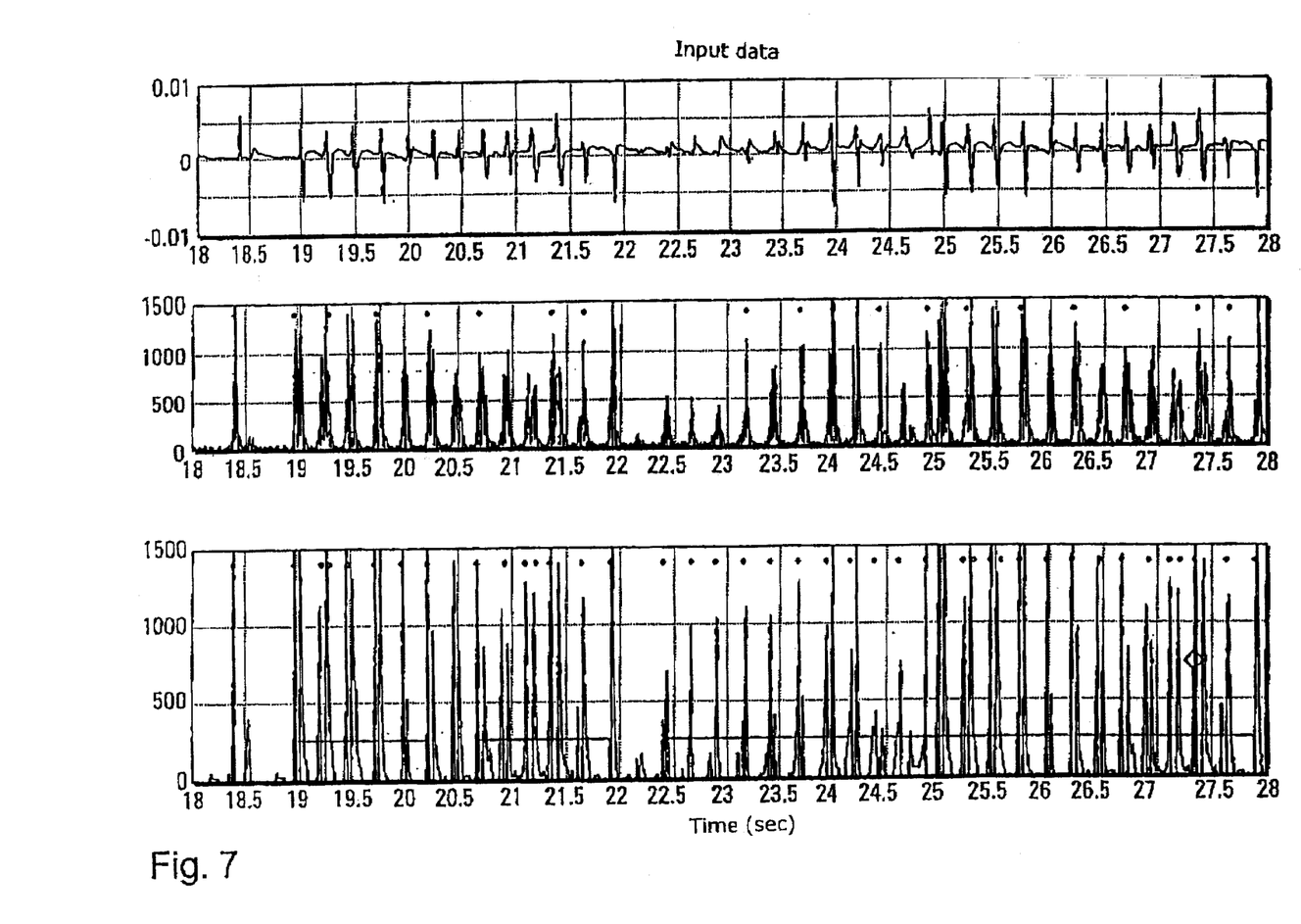
Figure 8:
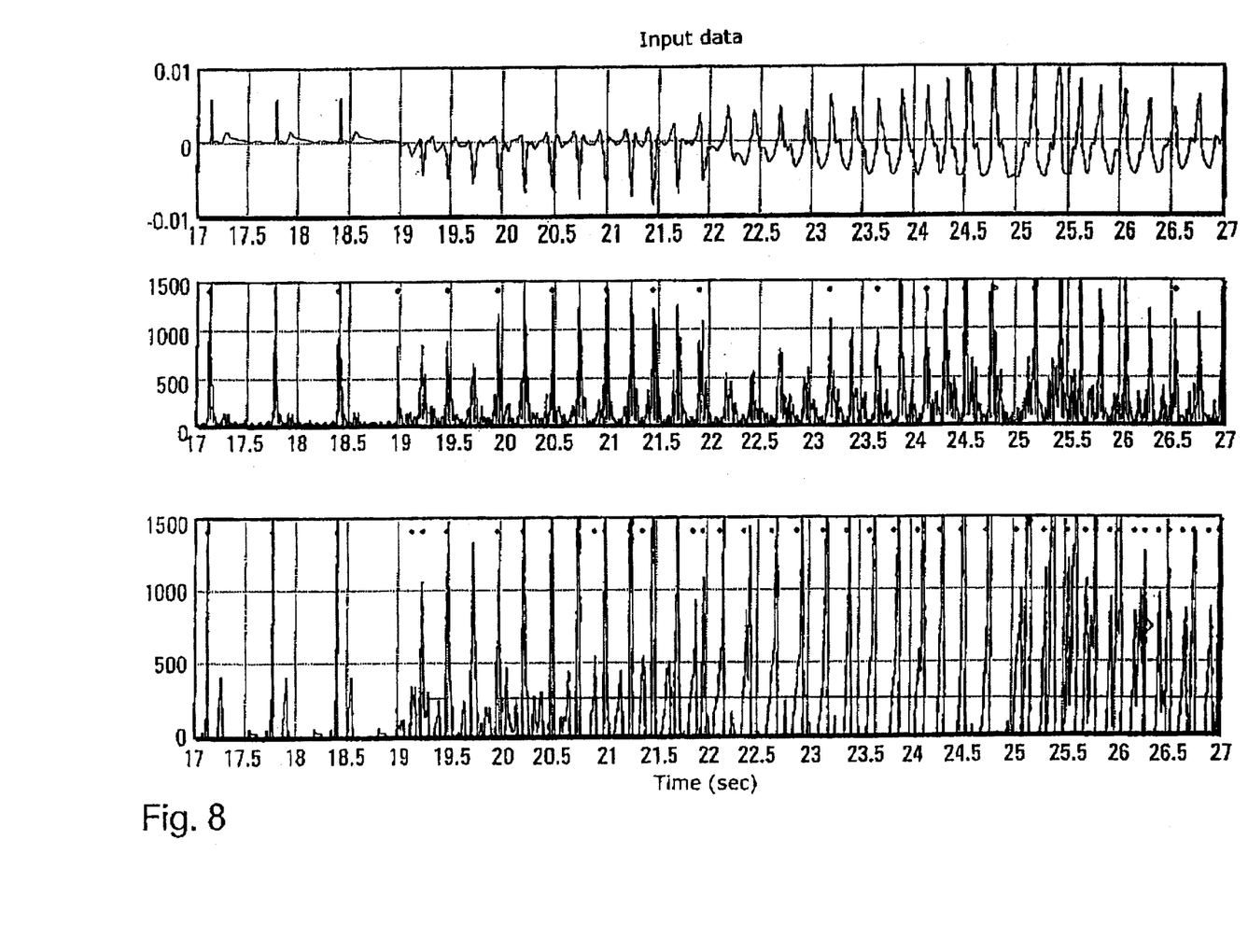
Figure 9:
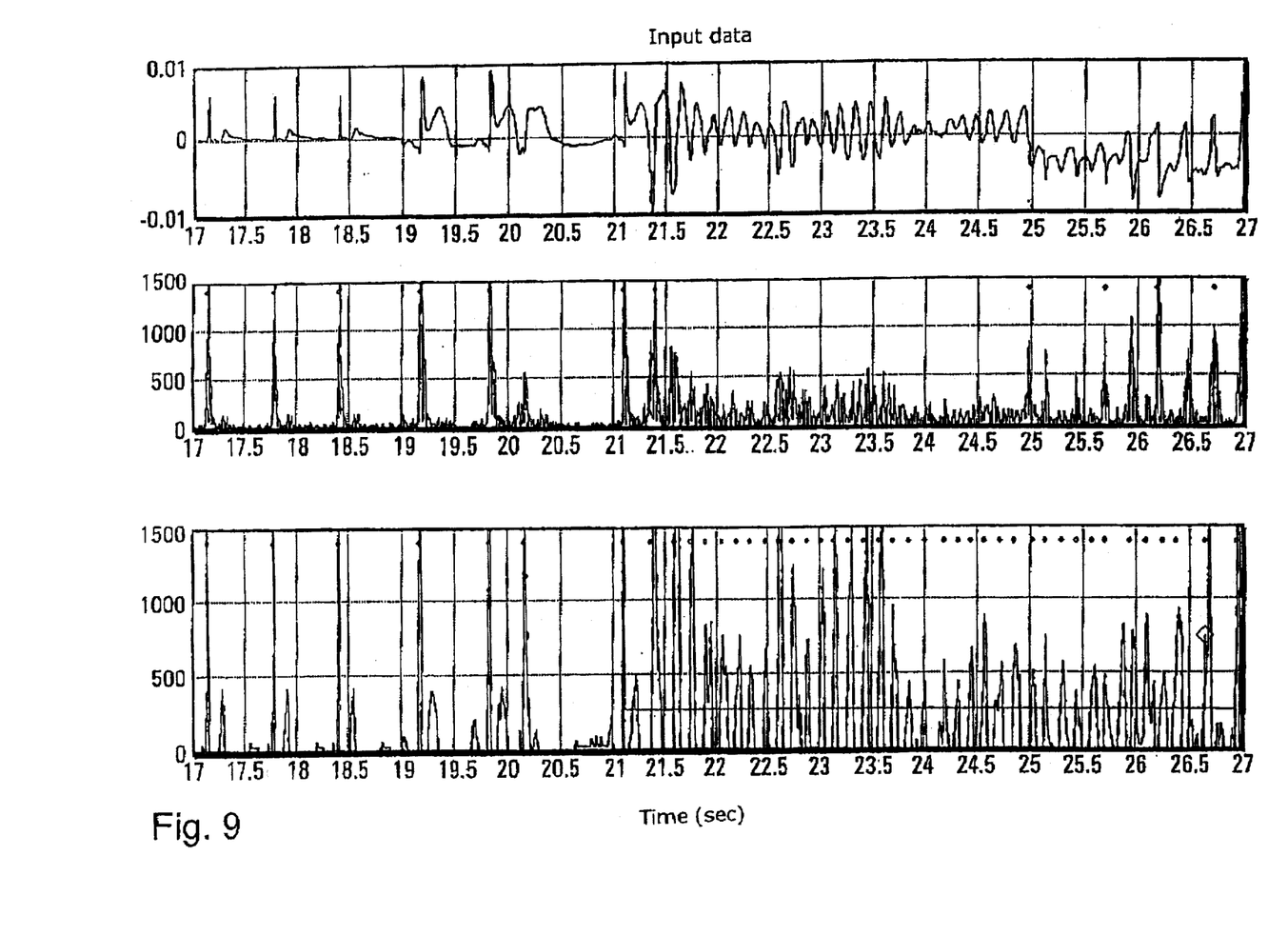
Figure 10:
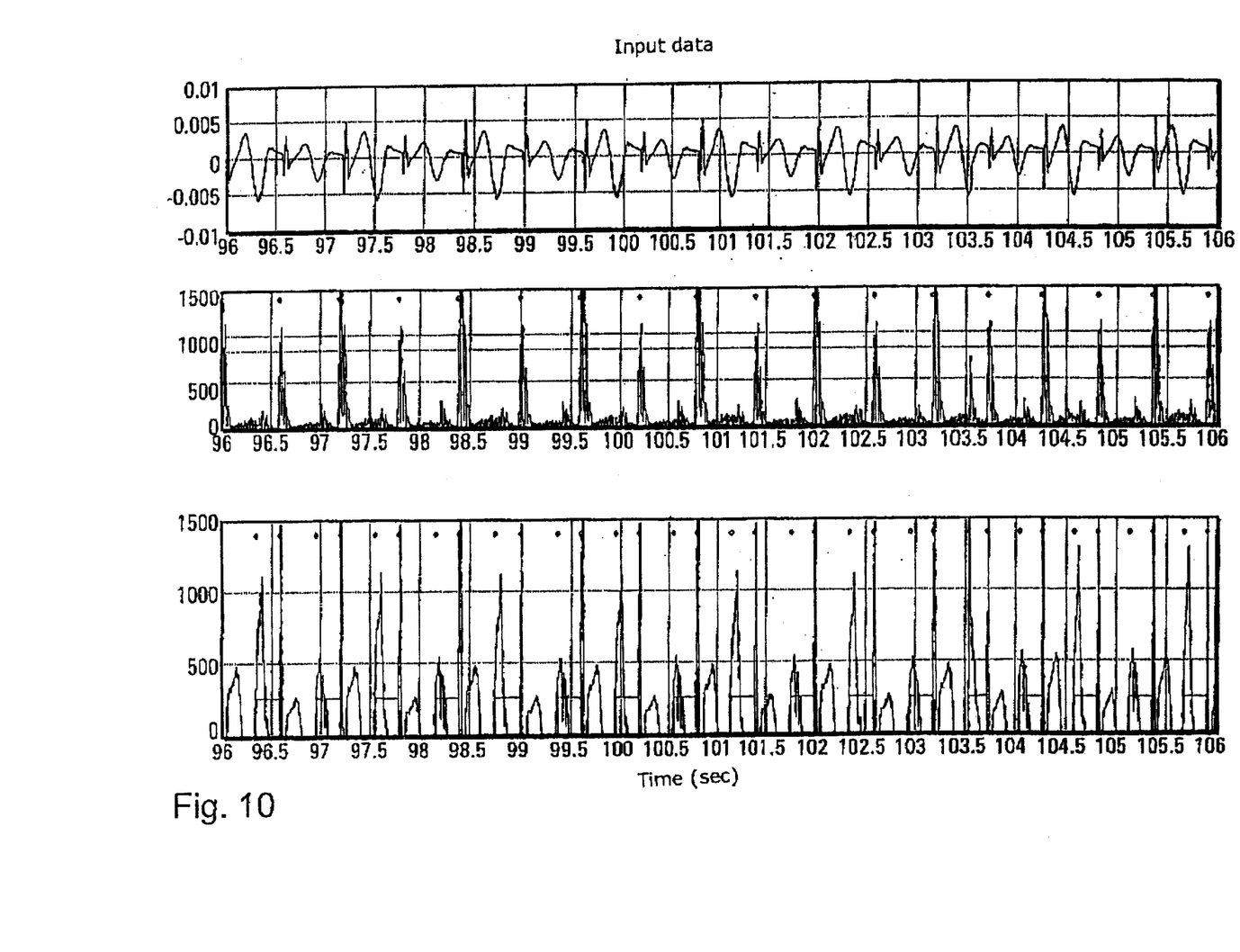
Figure 11:
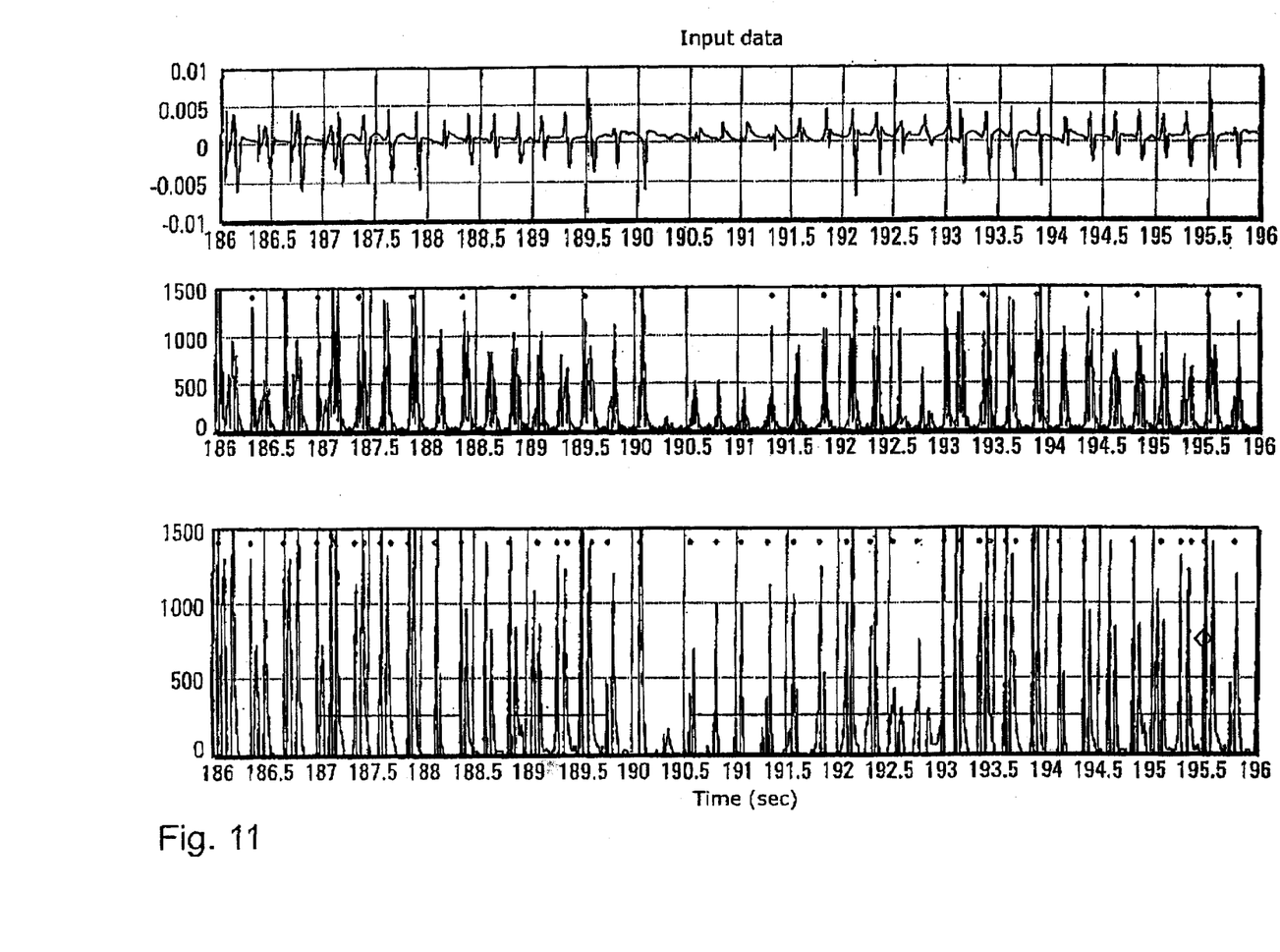

Of the five signal series shown in FIG. 5 the first is an example of a signal series as originates from the first detection means 14 while the second illustrated signal series represents a signal series which comes from the second detection means 16, as occurs at the output of the masking unit 64. All those signals of the first signal series which do not have any counterpart in the second signal series are detected by the coincidence transfer unit 68 and integrated by the coincidence transfer masking unit 68 into the signal series which comes from the masking unit 64, so that the third series shown in FIG. 5 is produced. The fourth signal series in FIG. 5 represents the second masking times which are triggered by the coincidence transfer masking unit 68. At the output of the coincidence transfer masking unit 68 there is then a signal which corresponds to the fifth signal series shown in FIG. 5. That signal is subjected to further processing to generate a fibrillation recognition signal by the identification unit 60, using the above-described '36 out of 48' criterion.

The diagrams illustrated in FIGS. 6 through 11 correspond in their nature to the diagrams shown on the right-hand side in FIG. 3. This means that the first of the respective three diagrams represents a measurement signal, the second diagram therebeneath represents the pre-processed measurement signal at the input of the threshold value detector 38 of the first detection means 14 and the first marker signals outputted by the threshold value detector 38. The first marker signals are illustrated in the form of rhombuses at the upper edge of each of the second diagrams. The third of the three diagrams in each case represents on the one hand the preprocessed measurement signal corresponding to the measurement signal shown in the first diagram, at the input of the threshold value detector 50 of the second detection means 16. In addition that third diagram shows in rhombus form at the upper edge thereof the second marker signals which are outputted by the threshold value detector 50. A line which is drawn as a continuous line in a portion of the third diagram in each case in the lower third thereof characterises intervals which correspond to an increased heart rate. A rhombus which is shown in large form in the middle of each of the third diagrams represents the fibrillation recognition signal which is respectively outputted by the signal processing apparatus 10.

What is claimed is:

1. An apparatus for processing physiological signals, comprising
   a unit for picking up physiological measurement signals, in particular for picking up electrical signals of a heart,
   a first detection means connected to the signal pick-up unit, comprising a signal processing means such as a filter and a first threshold value store and a first comparison unit that is connected thereto and that outputs a first marker signal when the amplitude of the measurement signal exceeds a threshold value stored in the first threshold value store,
   a second detection means connected to the signal pick-up unit and including a second threshold value store and a second comparison unit that is connected thereto and that outputs a second marker signal when the amplitude of the measurement signal exceeds a threshold value stored in the second threshold value store, and
   an evaluation unit that is connected to the first and second detection means for taking over a respective series of the first and second marker signals and for processing the series of marker signals to afford a single filtered series of combined marker signals, for analysis of the time succession of the marker signals, in particular the intervals between marker signals of the filtered series, and output of a recognition signal which is dependent on the analysis.

2. The apparatus of claim 1 wherein the evaluation unit further comprises a counter that counts the marker signals or the intervals between marker signals within a predetermined portion of the filtered series of marker signals.

3. The apparatus of claim 2 wherein the first detection means further comprises a first absolute value unit that forms the absolute value of the measurement signal.

4. The apparatus of claim 3 wherein the first absolute value unit is connected upstream of the first comparison unit.

5. The apparatus of claim 3 wherein the second detection means further comprises a second absolute value unit which is adapted to form the absolute value of the measurement signal.

6. The apparatus of claim 5 wherein the second absolute value unit is connected upstream of the second comparison unit.

7. The apparatus of claim 1 wherein the signal pick-up unit further comprises a high pass filter with a limit frequency of the order of magnitude of 10 Hz.

8. The apparatus of claim 7 wherein the signal processing means of the first detection means has a high pass filter with a limit frequency that is above that of the high pass filter of the signal pick-up unit.

9. The apparatus of claim 8 wherein the limit frequency of the high pass filter of the signal processing means is in the range of about 20 to about 30 Hz.

10. The apparatus of claim 1 wherein the second detection means further comprises a high pass filter with a limit frequency of the order of magnitude of 10 Hz.

11. The apparatus of claim 10 wherein the signal processing means of the first detection means has a high pass filter with a limit frequency that is above that of the second detection means.

12. The apparatus of claim 11 wherein the limit frequency of the high pass filter of the signal processing means is in the range of about 20 to about 30 Hz.

13. The apparatus of claim 1 wherein the evaluation unit takes over series of first and second marker signals in a time-correlated manner, such evaluation unit further comprising a logic unit for forming from the two series a single output series of the marker signals, which contains both all first and also all second marker signals in ordered relationship with respect to time in accordance with their association with the measurement signals to be triggered, wherein first and second measurement signals are combined within a predeterminable coincidence time of about 50 ms before and/or after a first marker signal to afford a marker signal of the output series.

14. The apparatus of claim 13 wherein the evaluation unit further comprises a filter unit that is connected to the logic unit and forms a filtered series of marker signals in such a way that the combined series contains only such marker signals lying outside a masking time, which begins with each marker signal from the series of second marker signals.

15. The apparatus of claim 14 wherein the masking time is about 300 ms.

16. The apparatus of claim 14 wherein the evaluation unit further comprises an identification unit, said identification unit comprising:
    a means for determining a time interval between two adjacent marker signals of the filtered series of marker signals,
    a comparison interval store for a comparison interval time duration,
    a means for comparing time intervals which is connected to the interval determining means and the comparison interval store and detects those intervals of the filtered series of marker signals, which are shorter than the comparison interval time duration,
    a counter, connected to the interval comparison means, to determine the number of marker signals within a portion of the filtered series of marker signals or intervals between two respective adjacent marker signals and the number of those intervals which are shorter than the comparison interval time duration, and
    a signal generator, connected to the interval counting unit and a quotient store, the signal generator outputting a signal when the proportion of the intervals that are shorter than the comparison interval time duration exceeds a proportion, stored in the quotient store, of the total number of intervals of a portion of the filtered series.

17. The apparatus of claim 1 wherein the first detection means further comprises a first absolute value unit that forms the absolute value of the measurement signal.

18. The apparatus of claim 17 wherein the first absolute value unit is connected upstream of the first comparison unit.

19. The apparatus of claim 17 wherein the second detection means further comprises a second absolute value unit which is adapted to form the absolute value of the measurement signal.

20. The apparatus of claim 19 wherein the second absolute value unit is connected upstream of the second comparison unit.

21. The apparatus of claim 1 wherein the evaluation unit takes over series of first and second marker signals in a time-correlated manner, such evaluation unit further comprising:
    a means for recognizing coincidences that outputs a coincidence signal when one of the first marker signals falls outside the first refractory time and one of the second marker signals falls outside the second noise suppression period in a predeterminable coincidence period;
    a masking means that is connected to the coincidence recognition means and that masks those of the second marker signals for further signal processing, which within a first masking time follow a second marker signal which led to a coincidence signal,
    a means for transferring coincidences that is connected to the coincidence recognition means and that adds the first of the first marker signals which follows a coincidence signal outside the first noise suppression period and within a transfer period, while retaining the time relationship of the series of the second marker signals, and thus to form a modified series of marker signals, and
    a coincidence transfer masking means connected to the coincidence transfer means that masks out of the modified series of marker signals all those marker signals that within a second masking time follow a marker signal added by the coincidence transfer means, in order thereby to form a combined series of marker signals.

22. The apparatus of claim 21 wherein the evaluation unit further comprises an identification unit, said identification unit comprising:
    a means for determining a time interval between two adjacent marker signals of the filtered series of marker signals,
    a comparison interval store for a comparison interval time duration,
    a means for comparing time intervals which is connected to the interval determining means and the comparison interval store and detects those intervals of the filtered series of marker signals, which are shorter than the comparison interval time duration,
    a counter, connected to the interval comparison means, to determine the number of marker signals within a portion of the filtered series of marker signals or intervals between two respective adjacent marker signals and the number of those intervals which are shorter than the comparison interval time duration, and
    a signal generator, connected to the interval counting unit and a quotient store, the signal generator outputting a signal when the proportion of the intervals that are shorter than the comparison interval time duration exceeds a proportion, stored in the quotient store, of the total number of intervals of a portion of the filtered series.

23. The apparatus of claim 21 wherein the predeterminable coincidence time is about 50 ms.

24. The apparatus of claim 21 wherein the first masking time is about 300 ms.

25. The apparatus of claim 21 wherein the transfer period is about 300 ms.

26. The apparatus of claim 21 wherein the second masking time is about 300 ms.

27. The apparatus of claim 1 wherein the first detection means further comprises a first noise limiting unit to suppress further processing of the measurement signal within a predeterminable first noise suppression time duration of the order of magnitude of 125 ms after each signal value of the measurement signal which results in a second measurement signal and is retriggerable thereby.

28. The apparatus of claim 27 wherein the second detection means further comprises a second noise limiting unit to suppress further processing of the measurement signal within a predeterminable second noise suppression time duration of 50 ms after each signal value of the measurement signal which leads to a second marker signal.

29. The apparatus of claim 28 wherein the first detection means further comprises a timer for a first refractory time to trigger a predeterminable absolute refractory time that is of an order of magnitude of 150 ms after each signal value that is outside the first refractory time and that results in a first marker signal, and wherein the first detection means suppresses further processing of the measurement signal within the absolute refractory time.

30. The apparatus of claim 29 wherein the first refractory timer triggers a total refractory time that is greater than the absolute refractory time, which includes same and which is about 300 ms, and wherein the first detection means suppresses further processing of first marker signals within the refractory time.

31. The apparatus of claim 30 wherein the total refractory time that is greater than 300 ms.

32. The apparatus of claim 30 wherein the second detection means further comprises a timer for a second refractory time, which is adapted to trigger a predeterminable refractory time which is shorter than or equal to the refractory time of the first detection means after each signal value which lies outside the second refractory time and which leads to a second marker signal, and that the second detection means suppresses further processing of second marker signals within the refractory time.

33. The apparatus of claim 32 further comprising at least one edge detection means connected to the first and/or second noise limiting unit and/or the first and/or the second refractory timer, wherein each said edge detection means detects a rising signal edge of the measurement signal that is associated with a measurement signal value that is associated with a first or a second marker signal, so that the respective noise suppression time duration and/or the respective refractory time begins with the detected signal edge.

34. The apparatus of claim 33 wherein said at least one edge detection means is connected to the first and/or the second threshold value store and detects a positive signal edge by a rising threshold value passage of the measurement signal.

35. The apparatus of claim 1 wherein the signal pick-up unit has a decimator that samples the measurement signal at a first clock rate and outputs at a second clock rate a respective new sample value for the measurement signal.

36. The apparatus of claim 35 wherein the signal pick-up unit further comprises an analog/digital converter that converts each analog sample value, in particular the output values of the decimator, into a digital value, so that at the output of the analog/digital converter there is a time-discrete series of digital values which correspond to the measurement signal.

37. The apparatus of claim 36 wherein the first clock rate is about 8 times faster than the second clock rate.

38. The apparatus of claim 37 wherein the first clock rate is about 4096 ms.

39. The apparatus of claim 36 wherein the signal pick-up unit further comprises a means for averaging to form a sliding average of the measurement signal.

40. The apparatus of claim 39 wherein the first detection means comprises a signal amplifier with an adaptable gain factor.

41. The apparatus of claim 40, further comprising a stimulation unit to deliver pulses suitable for heart stimulation, wherein the signal amplifier increases a gain factor thereof when the stimulation unit delivers a pulse and/or the series of second marker signals has a marker signal within a predetermined period of time prior to delivery of a pulse.

42. The apparatus of claim 41, further comprising an activation unit, connected to the second detection means and the signal amplifier so that the activation unit activates the second detection means when the gain factor of the signal amplifier increases.

43. The apparatus of claim 41 wherein the predetermined time interval is about 20 ms.

44. The apparatus of claim 41, further comprising an activation unit, connected to the first and the second detection means so that the activation unit activates the second detection means when the series of the first marker signals exceeds a predetermined frequency of marker signals.

45. The apparatus of claim 44 wherein the second detection means comprises a signal store, connected through an analog/digital converter to the signal pick-up unit, which stores at least one respective current portion of the measurement signal.

46. The apparatus of claim 44 wherein the predetermined frequency of marker signals is about 140 per minute.

* * * * *